(12) United States Patent
Samain (10) Patent No.: US 11,166,884 B2
(45) Date of Patent: Nov. 9, 2021

(54) ASSEMBLY CONTAINING AT LEAST ONE DYEING SUBSTRATE AND AT LEAST ONE SUBSTRATE COMPRISING ONE OR MORE PRESERVATIVES, DISPENSING MEANS, AND DYEING PROCESS

(71) Applicant: L'OREAL, Paris (FR)

(72) Inventor: Henri Samain, Bievres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/958,346

(22) PCT Filed: Dec. 21, 2018

(86) PCT No.: PCT/EP2018/086543
§ 371 (c)(1),
(2) Date: Jun. 26, 2020

(87) PCT Pub. No.: WO2019/129698
PCT Pub. Date: Jul. 4, 2019

(65) Prior Publication Data
US 2021/0059908 A1    Mar. 4, 2021

(30) Foreign Application Priority Data

Dec. 28, 2017    (FR) ...................................... 1763318

(51) Int. Cl.
*A61Q 5/10*    (2006.01)
*A61K 8/02*    (2006.01)
(Continued)

(52) U.S. Cl.
CPC .............. *A61K 8/0233* (2013.01); *A61K 8/22* (2013.01); *A61K 8/23* (2013.01); *A61K 8/411* (2013.01);
(Continued)

(58) Field of Classification Search
CPC ... A61Q 5/10; A61Q 8/23; A61K 8/22; A61K 8/411; A61K 8/415; A61K 2800/88;
(Continued)

(56) References Cited

U.S. PATENT DOCUMENTS

2016/0317399 A1* 11/2016 Samain ................ A61K 8/0204

FOREIGN PATENT DOCUMENTS

| EP | 1 695 689 A1 | 8/2006 |
|----|---|---|
| FR | 2 984 087 A1 | 6/2013 |

(Continued)

OTHER PUBLICATIONS

International Search Report and Written Opinion dated Feb. 27, 2019, issued in corresponding International Application No. PCT/EP2018/086543, filed Dec. 21, 2018, 12 pages.

*Primary Examiner* — Eisa B Elhilo
(74) *Attorney, Agent, or Firm* — Christensen O'Connor Johnson Kindness PLLC (57) ABSTRACT

Assembly containing at least one dyeing substrate and at least one protective substrate comprising one or more preservatives, dispensing means, and dyeing process The present invention relates to the field of dyeing keratin fibres and more particularly to the field of hair dyeing. The present invention relates to an assembly 2 containing at least one dyeing substrate 3, and at least one protective substrate 4a, 4b comprising one or more preservatives, and it being understood that the dyeing substrate(s) 3 are different from the protective substrate(s) 4a, 4b. The present invention also relates to a means for dispensing 1 the assembly 2, and also to a process for dyeing keratin fibres using said assembly 2.

16 Claims, 1 Drawing Sheet

(51) Int. Cl.
  *A61K 8/22* (2006.01)
  *A61K 8/23* (2006.01)
  *A61K 8/41* (2006.01)
  *A61K 8/46* (2006.01)
  *A61K 8/49* (2006.01)
  *A61K 8/73* (2006.01)

(52) U.S. Cl.
  CPC ............. *A61K 8/415* (2013.01); *A61K 8/46* (2013.01); *A61K 8/4973* (2013.01); *A61K 8/731* (2013.01); *A61Q 5/10* (2013.01); *A61K 2800/43* (2013.01); *A61K 2800/87* (2013.01)

(58) Field of Classification Search
  CPC ........ A61K 2800/4324; A61K 2800/87; A61K 8/46; A61K 8/731; A61K 8/4973; A61K 2800/43
  USPC .......................................................... 8/405
  See application file for complete search history.

(56) References Cited

FOREIGN PATENT DOCUMENTS

| | | | |
|---|---|---|---|
| WO | 98/46202 | A1 | 10/1998 |
| WO | 03/041531 | A1 | 5/2003 |
| WO | 2015/097307 | A1 | 7/2015 |

\* cited by examiner

ASSEMBLY CONTAINING AT LEAST ONE DYEING SUBSTRATE AND AT LEAST ONE SUBSTRATE COMPRISING ONE OR MORE PRESERVATIVES, DISPENSING MEANS, AND DYEING PROCESS

The present invention relates to the field of dyeing keratin fibres and more particularly to the field of hair dyeing.

The present invention relates to an assembly containing at least one dyeing substrate, and at least one protective substrate comprising one or more preservatives, and it being understood that the dyeing substrate(s) are different from the protective substrate(s).

The present invention also relates to a means for dispensing the assembly, and also to a process for dyeing keratin fibres using said assembly.

It is known practice to dye keratin fibres, in particular human keratin fibres such as the hair, to obtain "permanent" colourings with dye compositions containing oxidation dye precursors, which are generally known as oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colour modifiers, the latter being chosen especially from aromatic meta-diamines, meta-aminophenols, meta-diphenols and certain heterocyclic compounds such as indole or pyridine compounds. The variety of molecules used as oxidation bases and couplers allows a wide range of colours to be obtained.

Standard oxidation dyeing processes consist generally in applying, to keratin fibres, a dye composition comprising oxidation bases or a mixture of oxidation bases and couplers with hydrogen peroxide ($H_2O_2$ or aqueous hydrogen peroxide solution), as oxidizing agent, in leaving it to diffuse, and then in rinsing said fibres. The colourings resulting therefrom are generally permanent, strong and resistant to external agents, in particular to light, bad weather, washing, perspiration and rubbing.

Unfortunately, oxidation precursors are compounds that are relatively reactive to oxygen, and in particular to atmospheric oxygen. The oxidation precursors can thus pose problems with regard to the storage and preservation over time of conventional oxidation dyeing agents.

Thus, it is a well-known practice to add preserving compounds to dye compositions, in order to slow down the oxidation of the oxidation precursors.

However, an increasing number of users are seeking dye compositions referred to as "less chemical" and "more environmentally friendly", in point of fact some users may see preserving compounds in a negative way, in particular as compounds that are harmful to their health or to the environment.

There is therefore a real need to have available agents for oxidation dyeing of keratin fibres which comprise little or no preservative, while at the same time exhibiting satisfactory preservation over time, in particular with respect to atmospheric oxygen, and which make it possible to dye keratin fibres in a manner which is intense and chromatic, with good colour build-up, which is stable with respect to light, and/or capable of resulting in colourings that are resistant to the various attacks that the fibres may be subjected to, such as bad weather, washing (shampoo washes) and perspiration.

These objectives are achieved with the present invention, the subject of which is in particular an assembly containing:
  at least one substrate for dyeing keratin fibres, in particular human keratin fibres such as the hair, comprising a surface coated with at least one layer constituted of a dye composition comprising one or more oxidation dyes; and
  at least one protective substrate, comprising a surface coated with at least one layer constituted of a composition comprising one or more preservatives;
  it being understood that said dyeing substrate(s) is (are) different from said protective substrate(s).

The assembly according to the invention has in particular the advantage that it can be easily and effectively preserved over time, in particular with respect to atmospheric oxygen. The assembly can be preserved both at ambient temperature or at a temperature below 0° C.

The assembly in particular allows the user to make use of the dyeing substrate at the last minute.

The assembly according to the invention also makes it possible to obtain colourings which are powerful and chromatic, with good build-up of the colour, which are sparingly selective and which are resistant with respect to external agents (such as shampoos, light, perspiration or bad weather).

In other words, the invention relates to an assembly of dyeing substrate(s) and protective substrate(s).

For the purposes of the present invention, the term "substrate" is intended to mean a support on which a dye composition (dyeing substrate) or a composition comprising one or more preservatives has been deposited.

A subject of the present invention is also a means for dispensing the assembly.

A subject of the present invention is also a process for the oxidation dyeing of keratin fibres, in particular human keratin fibres such as the hair, comprising:
  i) a step consisting in removing said protective substrate(s) from the assembly;
  ii) a step of applying, to said fibres, the dyeing substrate(s); and
  iii) a step of applying, to said fibres, an oxidizing aqueous composition comprising one or more chemical oxidizing agents, and optionally one or more alkaline agents.

The process for dyeing keratin fibres according to the invention advantageously makes it possible to deposit little, or even no, preservatives on the keratin fibres.

Other subjects, characteristics, aspects and advantages of the invention will emerge even more clearly on reading the description and the examples that follow.

For the purposes of the present invention and unless otherwise indicated:
  a "heteroaryl radical" represents a fused or non-fused, optionally cationic, 5- to 22-membered monocyclic or polycyclic group, comprising from 1 to 6 heteroatoms chosen from nitrogen, oxygen, sulfur and selenium atoms, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthinyl or thioxanthinyl;

an "aryl" radical represents a monocyclic or fused or non-fused polycyclic carbon-based group, comprising from 6 to 22 carbon atoms, at least one ring of which is aromatic; preferentially, the aryl radical is a phenyl, biphenyl, naphthyl, indenyl, anthracenyl or tetrahydronaphthyl;

the "aryl" or "heteroaryl" radicals or the aryl or heteroaryl part of a radical may be substituted with at least one substituent borne by a carbon atom, chosen from:
- a $C_1$-$C_6$ and preferably $C_1$-$C_4$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
- a halogen atom;
- a hydroxyl or thiol group;
- a $C_1$-$C_6$ alkoxy or $C_1$-$C_6$ alkylthio radical;
- a (poly)hydroxy($C_2$-$C_6$)alkoxy radical;
- an amino radical;
- a 5- or 6-membered heterocycloalkyl radical, preferentially morpholino, piperazino, piperidino or pyrolidino, which is optionally substituted with a ($C_1$-$C_4$) alkyl radical, preferentially methyl;
- a 5- or 6-membered heteroaryl radical, preferentially imidazolyl, optionally substituted with a ($C_1$-$C_4$) alkyl radical, preferentially methyl;
- an amino radical substituted with one or two identical or different $C_1$-$C_6$ alkyl radicals, optionally bearing at least:
  - a hydroxyl group,
  - an amino group optionally substituted with one or two optionally substituted $C_1$-$C_3$ alkyl radicals, said alkyl radicals possibly forming, with the nitrogen atom to which they are attached, a saturated or unsaturated, optionally substituted 5- or 7-membered heterocycle, optionally comprising at least one other nitrogen or non-nitrogen heteroatom,
  - a quaternary ammonium group —N⁺R'R"R'", M⁻ for which R', R" and R'", which may be identical or different, represent a hydrogen atom or a $C_1$-$C_4$ alkyl group and M⁻ represents an anionic counterion,
  - or an optionally cationic 5- or 6-membered heteroaryl radical, preferentially imidazolium, optionally substituted with a ($C_1$-$C_4$)alkyl radical, preferentially methyl;
- an acylamino radical (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical;
- a carbamoyl radical ((R)$_2$N—C(O)—) in which the R radicals, which may be identical or different, represent a hydrogen atom or a $C_1$-$C_4$ alkyl radical optionally bearing at least one hydroxyl group;
- an alkylsulfonylamino radical (R'—S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical, or a phenyl radical;
- an aminosulfonyl radical ((R)$_2$N—S(O)$_2$—) in which the R radicals, which may be identical or different, represent a hydrogen atom or a $C_1$-$C_4$ alkyl radical optionally bearing at least one hydroxyl group;
- a carboxyl radical in the acid or salified form (preferably salified with an alkali metal or a substituted or unsubstituted ammonium);
- a cyano group;
- a nitro or nitroso group;
- a polyhaloalkyl group, preferably trifluoromethyl;
- a cyclic or heterocyclic radical, or a non-aromatic part of an aryl or heteroaryl radical, may also be substituted with one or more oxo groups;
- an "alkyl radical" is a linear or branched $C_1$-$C_{10}$, in particular $C_1$-$C_8$, more particularly $C_1$-$C_6$ and preferably $C_1$-$C_4$ hydrocarbon-based radical;
- within the meaning of the invention, a "polymer" is understood to be a compound corresponding to the repetition of one or more units (these units resulting from compounds known as monomers). This or these unit(s) are repeated at least twice and preferably at least three times;
- the term "film-forming polymer" is intended to mean a polymer that is capable of forming, by itself or in the presence of an auxiliary film-forming agent, a macroscopically continuous deposit on a support, preferably a cohesive deposit, and better still a deposit of which the cohesion and mechanical properties are such that said deposit can be isolable and manipulable in isolation, for example when said deposit is prepared by pouring onto a non-stick surface, such as a Teflon-coated or silicone-coated surface;
- the limits of a range of values are included in that range, in particular in the expressions "between . . . and . . . " and "ranging from . . . to . . . ";
- the expression "at least one" is equivalent to the expression "one or more" and can be replaced therewith.

I. Assembly

According to the invention, the assembly comprises at least one substrate for dyeing keratin fibres, comprising a surface coated with at least one layer constituted of a dye composition comprising one or more oxidation dyes.

The dyeing substrate(s) may be in the form of an element in sheet form or in another embodiment.

According to one preferred embodiment, the dyeing substrate(s) are elements in sheet form.

The dyeing substrate(s) may be made of plastic, in particular thermoplastic, paper, metal, especially aluminium, a woven, a nonwoven of non-absorbent fibres, especially of cellulose or a derivative thereof, or polyamide 6,6.

Preferably, the dyeing substrate(s) are sheets of plastic, in particular of thermoplastic, or a nonwoven material of non-absorbent fibres, especially a nonwoven based on cellulose or a derivative thereof.

Preferentially, the dyeing substrate(s) are sheets of plastic, in particular of thermoplastic.

The dyeing substrate(s) may be constituted of a water-soluble material, which makes it possible, for example, to remove it by washing the hair.

The dyeing substrate(s) preferably comprise a superposition of a layer of a water-soluble material and a layer of a water-insoluble material, for example an aluminium sheet.

The dyeing substrate(s) may be designed to be able to be closed around a lock of hair. In this case, such dyeing substrates are, for example, provided with a fastening means for keeping it in such a state, for example an adhesive disposed close to one edge or a mechanical attachment relief.

Preferably, the dyeing substrate(s) have a basis weight ranging from 20 to 300 g/m² and even more preferentially ranging from 30 to 200 g/m².

The dyeing substrate(s) have in particular a thickness ranging from 40 to 1000 micrometres, preferably a thickness ranging from 40 to 400 micrometres and better still from 60 to 200 micrometres.

The dyeing substrate(s) may be opaque or transparent. Preferably, the dyeing substrate(s) are transparent, which facilitates their positioning on the hair, especially when it is desired to produce one or more patterns at a precise place on the lock or on the head of hair. In other words, the transparency of the dyeing substrate(s) facilitates the implementation of the dyeing process, especially in the production of coloured patterns, and improves its precision.

The dyeing substrate(s) according to the invention are preferably flexible and strong. Preferentially, the strength of the dyeing substrate(s) is greater than 300 kPa (standard TAPPI-T403).

Preferably, the dyeing substrate(s) are water-resistant. In particular, the water absorption of said element is measured by the COBB 60 test which corresponds to the capacity of said element to absorb water during contact for 60 seconds (the procedure of which is given by standard ISO 535, TAPPI-T411 measurement).

Thus, the dyeing substrate(s) absorb less than 100 g/m² and preferentially less than 40 g/m² of water.

Preferably, the dyeing substrate(s) are resistant to oily compounds. Thus, use may be made of a "food" paper, i.e. a complex of paper and of polymeric compound of the polyethylene type or of paper and paraffin, which is capable of acting as a barrier to water and to oils.

According to one preferred embodiment of the invention, the assembly is covered with a layer of adhesive composition. This adhesive layer makes it possible to improve the adhesion of the oxidation dye(s) within the surface of the assembly. Thus, the assembly is protected by carrying out processes used in paper varnishing techniques (oil varnish, acrylic varnish, etc.). Preferably, the assembly contains one or more oxidation dyes and is covered with a layer of aqueous or organic acrylic varnish composition. In other words, the assembly contains a layer containing one or more oxidation dyes and a layer of acrylic varnish, the two layers being juxtaposed one on the other.

The mass per unit area of the layer of acrylic varnish ranges from 1 to 10 g/m² and more particularly from 2 to 5 g/m².

According to one variant of the invention, the dyeing substrate(s) are treated, at the level of the surface coated with at least one layer constituted of a dye composition comprising one or more oxidation dyes, with an aqueous composition comprising one or more film-forming polymers which are soluble or water-dispersible in an aqueous or aqueous-alcoholic medium, chosen from:
(meth)acrylate or (meth)acrylic homopolymers such as:
  acrylic polymers, in particular the Acrymul AM 123 R sold by the company Protex,
  polyacrylic acids, in particular the Carbomer sold by the company SEPC Coatex,
  polymethacrylic acids, in particular the Salcare SC130 sold by the company BASF,
  sodium polymethacrylates, in particular the Darvan 7-N sold by the company Vanderbildt;
copolymers comprising at least one (meth)acrylate or (meth)acrylic monomer, such as:
  the dimethyldiallylammonium chloride/acrylic acid (95/5) copolymer in aqueous solution, in particular sold under the reference Merquat 295 by the company Nalco (Lubrizol),
  the methacrylic acid/ethyl acrylate copolymer, in particular sold under the reference Luviflex Soft by the company Aromat;
(co)polymers based on vinyl acetate, such as:
  the vinyl acetate/vinyl p-(tert-butyl) benzoate/crotonic acid (65/25/10) terpolymer, in particular the Mexomer PW sold by the company Chimex,
  the vinyl acetate/crotonic acid/vinyl neodecanoate terpolymer, in particular the Resyn 28-2930 sold by Akzo Nobel;
polysaccharides, such as polymers derived from cellulose, starch, sucrose;
gums, such as guar gums;
protein polymers, such as soya protein hydrolysates (in particular the Aqua Pro SP 1 sold by MGP Ingredients), wheat or maize protein hydrolysates;
and mixtures thereof.

Preferably according to this variant, the dyeing substrate(s) are dried, and there then remains a layer, comprising the film-forming polymer(s), which juxtaposes the layer comprising one or more oxidation dyes, and optionally also the adhesive layer. This layer comprising the film-forming polymer(s) may be thin, of about 2 g of dry matter/m², or thick, of about 200 g of dry matter/m²; more preferentially, said layer comprising the film-forming polymer(s) has between 5 and 100 g of dry matter/m².

As previously indicated, the assembly according to the invention comprises at least one substrate for dyeing keratin fibres, comprising a surface coated with at least one layer constituted of a dye composition comprising one or more oxidation dyes.

The oxidation dyes may be chosen from one or more oxidation bases, optionally in combination with one or more couplers. Preferably, the oxidation dyes comprise at least one oxidation base and at least one coupler.

By way of example, the oxidation bases are chosen from para-phenylenediamines, bis(phenyl)alkylenediamines, para-aminophenols, ortho-aminophenols and heterocyclic bases, and addition salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-paraphenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and addition salts thereof.

Among the heterocyclic bases, examples that may be mentioned include pyridine derivatives, pyrimidine derivatives and pyrazole derivatives.

Among the pyridine derivatives, mention may be made of the compounds described for example in patents GB 1 026 978 and GB 1 153 196, for instance 2,5-diaminopyridine, 2-(4-methoxyphenyl)amino-3-aminopyridine and 3,4-diaminopyridine, and addition salts thereof.

Other pyridine oxidation bases that are useful in the present invention are the 3-aminopyrazolo[1,5-a]pyridine oxidation bases or addition salts thereof described, for example, in patent application FR 2 801308. Examples that may be mentioned include pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof.

Among the pyrimidine derivatives, mention may be made of the compounds described, for example, in patents DE 2359399, JP 88-169571, JP 05-63124 and EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives, mention may be made of the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. Use may also be made of 4,5-diamino-1-(β-methoxyethyl)pyrazole.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

Preferably, the oxidation bases are chosen from para-phenylenediamine, 1-methyl-2,5-diaminobenzene, para-aminophenol, 1-hydroxyethyl-4,5-diaminopyrazole sulfate and 2,3-diaminodihydroxypyrazolone dimethosulfonate, the addition salts thereof and mixtures thereof.

The coupler(s) are advantageously chosen from those conventionally used for the dyeing of keratin fibres.

Among these couplers, mention may be made especially of meta-phenylenediamines, meta-aminophenols, meta-diphenols, naphthalene-basedcouplers and heterocyclic couplers, and also the addition salts thereof.

Examples that may be mentioned include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, a-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially chosen from the addition salts with an acid, such as hydrochlorides, hydrobromides, sulfates, citrates, succinates, tartrates, lactates, tosylates, benzenesulfonates, phosphates and acetates.

Preferably, the coupler(s) are chosen from resorcinol, 2-methylresorcinol, 5-N-(β-hydroxyethyl)amino-2-methylphenol, 2-methyl-5-aminophenol, 1-β-hydroxyethyloxy-2,4-diaminobenzene dihydrochloride and 3-aminophenol, the addition salts thereof, and mixtures thereof.

The oxidation dye(s) may be present on all or part of the surface of the dyeing substrate. Thus, the surface of the substrate may be entirely or partially covered with a layer containing the dye composition.

According to one particular embodiment of the invention, the dye preparation composition as defined hereinafter is deposited on part of the surface of the dyeing substrate and represents patterns, which, after contact with the keratin fibres and the aqueous oxidizing composition, will make it possible to produce the coloured patterns on said fibres. In other words, the oxidation dye(s) are deposited in the form of patterns on the surface of the dyeing substrate. Thus, the surface of the dyeing substrate comprises one or more layers constituted of the dye composition arranged in one or more particular geometrical forms, known as patterns, which, after reaction with the aqueous oxidizing composition, lead to the production of coloured patterns on said fibres.

The pattern(s) may have any form, especially a geometrical form.

Thus, the dye(s) are present on a part of the surface of the dyeing substrate and represent patterns having the desired form.

The dye composition may optionally also comprise one or more alkaline agents. The alkaline agents may be chosen from carbonates, alkanolamines such as monoethanolamine, diethanolamine, triethanolamine and derivatives thereof, oxyethylenated and/or oxypropylenated ethylenediamines, mineral or organic hydroxides, alkali metal silicates such as sodium metasilicates, amino acids, preferably basic amino acids such as arginine, lysine, ornithine, citrulline and histidine, and the compounds of formula (I) below:

in which:
W is a divalent $(C_1-C_8)$alkylene group, preferably a propylene group, optionally substituted especially with a hydroxyl group or a $C_1-C_4$ alkyl radical;
$R_a$, $R_b$, $R_c$ and $R_d$, which may be identical or different, represent a hydrogen atom or a $C_1-C_4$ alkyl or $C_1-C_4$ hydroxyalkyl radical.

The mineral or organic hydroxides, particularly the mineral or organic hydroxides are preferably chosen from i) hydroxides of an alkali metal, ii) hydroxides of an alkaline-earth metal, for instance sodium hydroxide or potassium hydroxide, iii) hydroxides of a transition metal, such as hydroxides of metals from groups III, IV, V and VI, iv) hydroxides of lanthanides or actinides, quaternary ammonium hydroxides and guanidinium hydroxide.

The hydroxide may be formed in situ, for instance guanidine hydroxide, formed by reacting calcium hydroxide with guanidine carbonate.

In particular, the alkaline agents used are solid in the dry state.

In a first variant of the invention, the alkaline agents are solid before their use in the dye preparation composition as defined hereinafter, and are preferably chosen from carbonates, mineral hydroxides such as soluble sodium or potassium hydroxides or silicates.

In another variant of the invention, the alkaline agents are chosen from alkanolamines, in particular monoethanolamine, diethanolamine and triethanolamine.

Said dye composition may optionally also comprise one or more organic solvents.

Organic solvents that may be mentioned include linear or branched and preferably saturated monoalcohols or diols, comprising 2 to 6 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol or propylene glycol monomethyl, monoethyl or monobutyl ethers; and also diethylene glycol alkyl ethers, especially $C_1-C_4$ alkyl ethers, for instance diethylene glycol monoethyl ether or monobutyl ether.

The assembly may also comprise at the surface of the dyeing substrate(s) a layer of one or more activators or catalysts. In particular, the substrate(s) preferably comprise a layer of one or more metal salts in a content ranging from 1% to 20% by weight relative to the weights of the oxidation dyes present in the dye preparation composition before deposition on the surface of the dyeing substrate.

The process for producing a dyeing substrate comprises at least one step of treating the surface thereof with at least one dye preparation composition containing one or more oxidation dyes; and optionally at least one step of drying said dyeing substrate.

It is understood, for the purposes of the invention, that the dye preparation composition used in the process for producing the dyeing substrate comprises one or more oxidation dyes as described previously for the dye composition.

It is also understood, for the purposes of the invention, that the dye preparation composition may optionally comprise one or more alkaline agents and/or one or more organic solvents as described previously for the compound(s) optionally present in the dye composition.

Preferably, the dye preparation composition comprises one or more oxidation dyes and one or more alkaline agents.

When the dye preparation composition is aqueous and contains one or more alkaline agents, the pH preferably ranges from 7.5 to 13, better still from 8 to 12 and even better still from 8 to 11.

The dye preparation composition intended to be deposited on the surface of a dyeing substrate may be liquid or in pulverulent form at ambient temperature, preferably liquid at ambient temperature.

The dye composition(s) present on the surface of the dyeing substrate may optionally result from successive treatments of the substrate with, on the one hand, one or more oxidation dyes, on the other hand, optionally one or more alkaline agents, and optionally one or more active agents as described previously.

The oxidation base(s) and optionally the coupler(s) may advantageously represent from 0.01% to 100% by weight, preferably from 1% to 50% by weight and better still from 5% to 40% by weight relative to the total weight of the dye preparation composition before deposition on the surface of the dyeing substrate.

The alkaline agent(s) may be present in a total content preferably ranging from 0.01% to 20% by weight relative to the total weight of the dye preparation composition before deposition on the surface of the dyeing substrate.

Said dye preparation composition may optionally also comprise one or more preservatives in a total content preferably of less than or equal to 2% by weight, more preferentially less than or equal to 1% by weight, even more preferentially of between 0.1% and 0.9% by weight, and even better still of between 0.2% and 0.8% by weight, relative to the total weight of the dye preparation composition before deposition on the surface of the dyeing substrate.

Preferably, at least one step of treating the surface of the dyeing substrate consists in depositing at least one dye preparation composition as defined previously by means of a printing method. In other words, the dye preparation composition(s) are printed on the surface of a dye substrate, that is to say using a printing process which makes it possible to obtain the dyeing substrate defined previously.

Once printed on the surface of the substrate, the dye composition(s) are dried.

The printing method which serves to deposit the dye preparation composition on the surface of a dyeing substrate may be a screen printing process, a flexography process, an offset printing process or a printing process using an inkjet printer or a laser printer.

Preferably, the process for preparing a dyeing substrate thus corresponds to a process for printing a dyeing substrate, in which at least one dye preparation composition as defined previously is applied to the dyeing substrate by screen printing, flexography, offset printing or printing with an inkjet printer.

Preferentially, at least one dye preparation composition as defined previously is applied to the dyeing substrate by screen printing, or by means of an inkjet printer.

More preferentially, the dye preparation composition as defined previously is printed onto the surface of the dyeing substrate by means of an inkjet printer.

Advantageously, in this embodiment by printing, the dyeing substrate(s) are elements in sheet form.

When the preparation process consists in using a printing process using a laser printer, then the dye preparation composition containing the oxidation dye(s) is in powder form.

According to one preferred embodiment of the invention, the process for preparing a dyeing substrate comprises at least one depositing step consisting in depositing at least one dye preparation composition onto the surface of the dyeing substrate covered with a layer of adhesive composition. This adhesive layer may cover all or part of the dyeing substrate. In particular, the adhesive layer may represent a pattern.

According to another preferred embodiment of the invention, the process for preparing a dyeing substrate as described previously comprises at least one depositing step consisting in partially depositing onto the surface of a dyeing substrate, via a printing method, at least one dye preparation composition containing one or more oxidation dyes.

In accordance with this other preferred embodiment, the oxidation dye(s) are deposited in the form of one or more patterns onto the surface of a dyeing substrate. In particular, the patterns may be squares, circles, ovals, ellipses or triangles, in the form of filled patterns or of lines surrounding these patterns. They may also be thick or thin, straight or curved lines, crossed lines, representing letters, stylized drawings or geometrical patterns. They may also be dotted lines or spots.

Once the dye preparation composition(s) have been deposited at the surface of the dyeing substrate, the substrate is then dried.

The dyeing substrate thus pretreated in accordance with the production process preferably dries within a period ranging from 5 minutes to 120 minutes, preferentially from 5 minutes to 90 minutes, more preferentially from 1 minute to 60 minutes and better still from 5 minutes to 60 minutes.

Preferably, the step of drying said dyeing substrate consists in leaving said substrate to dry in the open air.

Once the dyeing substrate has been prepared, it comprises a surface coated with at least one layer constituted of a dye composition comprising one or more oxidation dyes.

For the purposes of the present invention, the dye composition(s) have a total water content of less than 20% by weight, preferably less than or equal to 15% by weight, more preferentially less than or equal to 10% by weight, relative to the total weight of the dye composition.

The oxidation base(s) and optionally the coupler(s) may advantageously represent from 0.01% to 100% by weight, preferably from 1% to 50% by weight and better still from 4% to 40% by weight relative to the total weight of the dye composition.

The alkaline agent(s) may be present in the dye composition in a total content preferably ranging from 0.01% to 20% by weight relative to the total weight of the dye composition.

The preservative(s) may be present in the dye composition in a content preferably of less than or equal to 2% by weight, more preferentially less than or equal to 1% by weight, even more preferentially of between 0.1% and 0.9% by weight, and even better still of between 0.2% and 0.8% by weight, relative to the total weight of the dye composition.

According to the invention, the assembly comprises at least one protective substrate, comprising a surface coated with at least one layer constituted of a composition comprising one or more preservatives.

According to one particular embodiment of the invention, the preservative(s) may be contained:

in the protective substrate in sheet form (in this case, the sheet may be made of any material, such as the polyhydrosolubles described above, polyethylenes, polypropylenes, celluloids, plasticized PVCs, cellophanes). Preferably, the protective substrate(s) are sheets of polyethylene material;

or at the protective surface (i.e "borne" by the protective substrate in sheet form); in this case, it forms a film on a water-soluble or water-dispersible polymer sheet as described above, which is deposited onto a sheet of materials as described above, or in this case, two layers which form the protective substrate.

The protective substrate(s) have in particular a thickness ranging from 10 to 500 micrometres, preferably a thickness ranging from 40 to 250 micrometres and better still from 80 to 150 micrometres.

The protective substrate(s) may be opaque or transparent.

Preferably, the protective substrate(s) are opaque, and in particular opaque to ultraviolet radiation in order to provide better protection.

Preferably, the assembly comprises one or two protective substrates, each comprising a surface coated with at least one layer constituted of a composition comprising one or more preservatives.

As indicated previously, the protective substrate(s) comprise a surface coated with at least one layer constituted of a composition comprising one or more preservatives. In other words, the protective substrate(s) are pretreated with a composition comprising one or more preservatives.

The preservatives may be chosen from sulfur-bearing reducing agents, such as thiolated reducing agents, non-thiolated reducing agents; non-sulfur-bearing reducing agents; compounds capable of slowing down the oxidative condensation reaction; and mixtures thereof.

Advantageously, the thiolated sulfur-bearing reducing agents may be chosen from organic compounds comprising one or more mercapto (—SH) groups and preferably at least one other function chosen from carboxylic acid, amine, amide, ester and alcohol functions and mixtures thereof.

According to a preferred embodiment of the invention, the thiolated reducing agent(s) used according to the invention are chosen from those of formulae i-1 and also the organic or mineral acid or base salts thereof, optical isomers thereof and tautomers thereof, and the solvates such as hydrates; and/or mixtures thereof:

i-1 in which formulae i-1:

R represents:
  a linear or branched $(C_1$-$C_8)$alkyl, preferably $(C_1$-$C_6)$alkyl group which is optionally substituted, preferably substituted with one or more groups chosen from carboxy C(O)OH, (di)($C_1$-$C_4$)(alkyl) amino, hydroxyl —OH, thiol —SH; and/or optionally interrupted with one or more heteroatoms or groups chosen from —O—, —S—, —N(R''')—, C(O) or combinations thereof such as —O—C(O)—, —C(O)—O—, —N(R''')—C(O)—, or —C(O)—N(R''')—; with R''' representing a hydrogen atom or a $(C_1$-$C_6$)alkyl group; preferably a $(C_1$-$C_4)$ alkyl group; or a (hetero)aryl group optionally substituted especially with one or more hydroxyl, thiol or carboxy groups.

According to a particular embodiment of the invention, the thiolated reducing agent(s) are chosen from those of formula i-1 as defined previously, and also the organic or mineral acid or base salts thereof, optical isomers thereof and tautomers thereof, and the solvates such as hydrates; and/or the mixtures thereof, for which R represents a linear or branched $(C_1$-$C_8)$alkyl, preferentially $(C_1$-$C_6)$alkyl group,
  which is substituted with one or more groups chosen from carboxy C(O)OH, amino, hydroxyl —OH and thiol —SH; and/or
  which is optionally interrupted with one or more heteroatoms or groups chosen from —O—, —N(R''')—, C(O) or combinations thereof such as —O—C(O)—, —C(O)—O—, —N(R''')—C(O)—, or —C(O)—N(R''')—, with R''' representing a hydrogen atom or a $(C_1$-$C_6$)alkyl group, preferentially a $(C_1$-$C_4$)alkyl group.

More preferentially, R represents a linear or branched, uninterrupted $(C_1$-$C_8$)alkyl group, better still $(C_1$-$C_6$)alkyl group.

According to another particular embodiment of the invention, the thiolated reducing agent(s) are chosen from those of formula i-1 as defined previously, and also the organic or mineral acid or base salts thereof, optical isomers thereof and tautomers thereof, and the solvates such as hydrates; and/or the mixtures thereof, for which R represents:
  a phenyl group optionally substituted with one or more hydroxyl, thiol or carboxy groups; or
  a 5- to 10-membered, preferably 9- or 10-membered bicyclic, heteroaryl, comprising from 1 to 4 heteroatoms chosen from O, S or N, preferably N, optionally substituted with one or more hydroxyl or thiol groups.

Preferably, the thiolated reducing agent(s) are chosen from thioglycolic acid, thiolactic acid, cysteine, cysteamine, homocysteine, glutathione, thioglycerol, thiomalic acid, 2-mercaptopropionic acid, 3-mercaptopropionic acid, thiodiglycol, 2-mercaptoethanol, dithiothreitol, N-acetylcysteine, esters and amides of thioglycolic or thiolactic acids, especially glyceryl monothioglycolate; and also the organic or mineral acid or base salts thereof, optical isomers thereof, tautomers thereof, and the solvates such as hydrates; and mixtures of these compounds.

Preferentially, the thiolated reducing agent(s) are chosen from thioglycolic acid, thiolactic acid, cysteamine, and also the organic or mineral acid or base salts thereof, optical isomers thereof and tautomers thereof, and the solvates such as hydrates, and mixtures thereof. More preferentially still, the thiolated reducing agent(s) are chosen from thioglycolic acid, thiolactic acid, and mixtures thereof.

As indicated previously, the thiolated reducing agent(s) may be used especially in the form of salts, in particular alkali metal salts such as sodium and potassium salts, alkaline-earth metal salts, for example magnesium and calcium salts, ammonium salts, amine salts and amino alcohol salts. Ammonium thioglycolate may thus be used as thiol.

Advantageously, the non-thiolated sulfur-bearing reducing agent(s) may be chosen from sulfites, bisulfites, sulfinates, and mixtures thereof.

As sulfites, mention may be made of ammonium sulfites and bisulfites, and also from metal sulfites and bisulfites, in particular alkali metal or alkaline-earth metal sulfites and bisulfites, and even better still sodium sulfites and bisulfites.

Sulfinates that may be mentioned include sulfinic acid salts and benzenesulfinic acid salts, such as the sodium salts thereof. The sulfinic acid derivatives described in FR-A-2 814 948 may also be used. A preferred sulfinate compound is the disodium salt of 2-hydroxy-2-sulfinatoacetic acid.

Advantageously, the non-sulfur-bearing reducing agents may be chosen from sugars, reductones, hydrides, and mixtures thereof.

Sugars or "monosaccharides" that may be mentioned include ribose, glyceraldehyde, glucose, maltose, galactose, lactose and xylose.

Reductones that may be mentioned include ascorbic acid and erythorbic acid.

Hydrides that may be mentioned include boron hydrides such as sodium borohydride, lithium hydride and phosphorous hydride. Hydride precursors, and in particular boron hydrides, such as diborane, tetraborane, pentaborane, decaborane and dodecaborane, may be used.

As is known per se, the term "reductone" denotes a compound comprising an enediol structure —(HO)C=C(OH)— adjacent to a carbonyl group —C(O)—.

Thus, the organic reducing agent(s) of reductone type according to the present invention are preferably of general formula (IX) and also the salts thereof; and/or the mixtures thereof:

in which formula:
$R_1$ and $R_2$ independently of one another each denote a group containing at least one carbon and/or oxygen atom, $R_1$ and $R_2$ possibly forming with the three carbon atoms of the compound of formula (IX) a ring, which is preferably 5- or 6-membered, the additional constituent atoms of which are constituted of carbon and/or oxygen atoms.

Preferably, $R_1$ and $R_2$ form with the three carbon atoms of the compound of formula (IX) a 5-membered ring, the additional constituent atoms of which are constituted of carbon and/or oxygen atoms.

As indicated previously, the organic reducing agent(s) of reductone type of formula (IX) may be in acid form, or in the form of salts, especially in the form of salts of alkali metals such as sodium and potassium, or salts of alkaline-earth metals such as calcium and magnesium, or in the form of esters, especially of $C_8$ to $C_{30}$ fatty acids.

Preferentially, the organic reducing agent(s) of reductone type of formula (IX) are lactones.

According to a preferred embodiment of the invention, the organic reducing agent(s) of reductone type are chosen from reductic acid, ascorbic acid, erythorbic acid or isoascorbic acid, and also salts thereof such as sodium or potassium salts, ascorbyl palmitate, and/or mixtures thereof.

More preferentially, the organic reducing agent(s) of reductone type are chosen from ascorbic acid, erythorbic acid, and the salts of these compounds, especially the sodium or potassium salts.

Advantageously, the compound(s) capable of slowing down the oxidative condensation reaction may be chosen from S-gluconolactone; sodium gluconate; potassium gluconate; calcium gluconate; potassium bitartrate; sodium acetate; sorbitol; acids such as ethylenediaminetetraacetic acid (EDTA), citric acid, phosphoric acid, and tartaric acid.

According to one preferred embodiment of the invention, the preservative(s) are chosen from sulfites, bisulfites, sulfinates, sugars, hydrides, thiolated sulfur-bearing reducing agents, organic reducing agents of reductone type, agents capable of slowing down the oxidative condensation reaction, and mixtures thereof; preferably, the preservative(s) are chosen from sulfites, bisulfites, thiolated reducing agents, organic reducing agents of reductone type, agents capable of slowing down the oxidative condensation reaction, and mixtures thereof.

According to one very preferred embodiment of the invention, the preservative(s) are chosen from ammonium sulfites and bisulfites, alkali metal or alkaline-earth metal sulfites and bisulfites, reductic acid, ascorbic acid, erythorbic or isoascorbic acid, thioglycolic acid, thiolactic acid, cysteine, cysteamine, ethylenediaminetetraacetic acid (EDTA), citric acid, and mixtures thereof.

The protective substrate(s) as defined previously can be produced according to a production process comprising at least one step of depositing, onto the surface(s) of a protective substrate, at least one aqueous preparation composition, termed preservative preparation composition, containing one or more preservatives as described previously.

The thiolated reducing agent(s) may be present in a total content preferably ranging from 0.5% to 60% by weight, preferentially from 1% to 50% by weight, more particularly from 4% to 45% by weight, even better still from 10% to 40% by weight relative to the total weight of the preservative preparation composition before deposition on the surface of the protective substrate.

Preferably, the non-thiolated reducing agent(s) may be present in a total amount ranging from 0.5% to 60% by weight, preferentially from 1% to 50% by weight, more particularly from 4% to 45% by weight, even better still from 10% to 40% by weight relative to the total weight of the preservative preparation composition before deposition on the surface of the protective substrate.

Preferably, the sulfite and/or bisulfite content is between 0.1% and 20% by weight, preferentially from 0.5% to 15% by weight, more particularly from 1% to 12% by weight, even better still from 2% to 10% by weight relative to the total weight of the preservative preparation composition before deposition on the surface of the protective substrate.

Preferably, the non-sulfur-bearing reducing agent(s) may be present in a total amount ranging from 0.5% to 60% by weight, preferentially from 1% to 50% by weight, more particularly from 4% to 45% by weight, even better still from 10% to 40% by weight relative to the total weight of the preservative preparation composition before deposition on the surface of the protective substrate.

Preferably, the compound(s) capable of slowing down the oxidative condensation reaction may be present in a content of less than or equal to 2% by weight, preferentially less than or equal to 1% by weight, even better sill ranging from 0.05% to 0.2% by weight relative to the total weight of the preservative preparation composition before deposition on the surface of the protective substrate.

Once deposited on the surface(s) of the protective substrate, the preservative preparation composition(s) containing one or more preservatives are dried.

The protective substrate thus pretreated in accordance with the production process preferably dries within a period ranging from 5 minutes to 120 minutes, preferentially from 5 minutes to 90 minutes, more preferentially from 1 minute to 60 minutes and better still from 5 minutes to 60 minutes.

Preferably, the step of drying said protective substrate consists in leaving said substrate to dry in the open air.

Once the protective substrate has been prepared, it comprises a surface coated with at least one layer constituted of a preservative composition comprising one or more preservatives.

For the purposes of the present invention, the preservative composition has, at the surface of the protective substrate once prepared, a total water content of less than 20% by weight, preferably less than or equal to 15% by weight, more preferentially less than or equal to 10% by weight, relative to the total weight of said composition.

Preferably, the thiolated reducing agent(s) are present in the preservative composition in a total amount ranging from 0.5% to 60% by weight, preferentially from 1% to 50% by weight, more particularly from 4% to 45% by weight and even better still from 10% to 40% by weight relative to the total weight of the preservative composition.

Preferably, the non-thiolated reducing agent(s) are present in the preservative composition in a total amount ranging from 0.5% to 60% by weight, preferentially from 1% to 50% by weight, more particularly from 4% to 45% by weight and even better still from 10% to 40% by weight relative to the total weight of the preservative composition.

Preferably, the total sulfite and/or bisulfite content present in the preservative composition is between 0.1% and 20% by weight, preferentially from 0.5% to 15% by weight, more particularly from 1% to 12% by weight, even better still from 2% to 10% by weight relative to the total weight of the preservative composition.

Preferably, the non-sulfur-bearing reducing agent(s) are present in the preservative composition in a total amount ranging from 0.5% to 60% by weight, preferentially from 1% to 50% by weight, more particularly from 4% to 45% by weight and even better still from 10% to 40% by weight relative to the total weight of the preservative composition.

Preferably, the compound(s) capable of slowing down the oxidative condensation reaction may be present in the preservative composition in a total content of less than or equal to 2% by weight, preferentially less than or equal to 1% by weight, even better still ranging from 0.05% to 0.2% by weight relative to the total weight of the preservative composition.

Preferably, the preservative(s) are present in the preservative composition in a total amount ranging from 0.1% to 60% by weight, preferentially from 4% to 40% by weight, more particularly from 5% to 30% by weight and even better still from 8% to 20% by weight relative to the total weight of the preservative composition comprising the preservative(s).

According to one preferred embodiment of the invention, the protective substrate(s) are elements in sheet form, and are prepared by deposition, onto one of the surfaces or onto several surfaces, of at least one preservative preparation composition comprising one or preservative(s) as described previously.

According to another preferred embodiment of the invention, the protective substrate(s) are prepared by deposition, onto one of their surfaces or onto several surfaces, of a preservative preparation composition comprising one or more preservative(s) as described previously and a total amount of preservative(s) ranging from 1% to 60% by weight, more preferentially from 2% to 40% by weight, relative to the total weight of the preservative preparation composition before deposition on the surface of the protective substrate.

According to the present invention, the dyeing substrate(s) are in contact, preferably directly in contact, with the protective substrate(s), or the dyeing substrate(s) and the protective substrate(s) are separated from one another.

According to a first preferred embodiment of the invention, the dyeing substrate is directly in contact and entirely covered with the protective substrate, said protective substrate being detachable. For this purpose, the edges of the dyeing substrate and of the protective substrate are bonded together by means of a fastening means, especially an adhesive, which may be produced via any type of method, especially by heat sealing.

Thus, good cohesion is ensured between the protective substrate and the dyeing substrate.

According to a second preferred embodiment of the invention the dyeing substrate is included between two protective substrates and in contact therewith, said protective substrates being detachable and placed on either side of the dyeing substrate. In other words, the dyeing substrate is sandwiched between the two protective substrates. For this purpose, the edges of the dyeing substrate and of the protective substrates are bonded together by means of a fastening means, especially an adhesive, which may be produced via any type of method, especially by heat sealing. Thus, good cohesion is ensured between the protective substrates and the dyeing substrate.

According to a third preferred embodiment of the invention, a protective substrate partially or totally, preferably totally, envelops said dyeing substrate, preferably in such a way that the protective substrate forms a hermetic packaging defining above the dyeing substrate an oxygen-free space (under vacuum or under an inert atmosphere).

According to this embodiment, a second protective substrate may optionally be in direct contact with the dyeing substrate and may entirely cover it, said second protective substrate being detachable.

According to a fourth preferred embodiment of the invention, the dyeing substrate and a protective substrate are separated from one another by a layer, termed polymer layer, comprising one or more film-forming polymers which are soluble or water-dispersible, in an aqueous or aqueous-alcoholic medium, chosen from:
  (meth)acrylate or (meth)acrylic homopolymers such as:
    acrylic polymers, in particular the Acrymul AM 123 R sold by the company Protex,
    polyacrylic acids, in particular the Carbomer sold by the company SEPC Coatex,
    polymethacrylic acids, in particular the Salcare SC130 sold by the company BASF,
    sodium polymethacrylates, in particular the Darvan 7-N sold by the company Vanderbildt;
  copolymers comprising at least one (meth)acrylate or (meth)acrylic monomer, such as:
    the dimethyldiallylammonium chloride/acrylic acid (95/5) copolymer in aqueous solution, in particular sold under the reference Merquat 295 by the company Nalco (Lubrizol),
    the methacrylic acid/ethyl acrylate copolymer, in particular sold under the reference Luviflex Soft by the company Aromat;
  (co)polymers based on vinyl acetate, such as:
    the vinyl acetate/vinyl p-(tert-butyl) benzoate/crotonic acid (65/25/10) terpolymer, in particular the Mexomer PW sold by the company Chimex,
    the vinyl acetate/crotonic acid/vinyl neodecanoate terpolymer, in particular the Resyn 28-2930 sold by Akzo Nobel;
  polysaccharides, such as polymers derived from cellulose, starch, sucrose;

gums, such as guar gums;

protein polymers, such as soya protein hydrolysates (in particular the Aqua Pro SP 1 sold by MGP Ingredients), wheat or maize protein hydrolysates;

and mixtures thereof.

Preferably according to this fourth preferred embodiment of the invention, a layer of dry matter at the surface of the dyeing substrate(s), comprising the film-forming polymer(s), juxtaposes the layer comprising one or more oxidation dyes, and optionally also the adhesive layer. This layer comprising the film-forming polymer(s) may be thin, of about 2 g of dry matter/m$^2$, or thick, of about 200 g of dry matter/m$^2$; more preferentially, said layer comprising the film-forming polymer(s) has between 5 and 100 g of dry matter/m$^2$.

According to a fifth preferred embodiment of the invention, the dyeing substrate and the protective substrate are separated from one another by an element in openwork sheet form, that is say perforated by holes which pierce right through, on either side, the element in openwork sheet form and which are spaced out from one another by a plastic.

In accordance with these embodiments, the dyeing substrate is preferably free of preservatives.

In other words, the dye composition intended to be deposited on the surface of a dyeing substrate contains no preservatives or contains them in a content of less than 2% by weight, preferably less than 1% by weight, more preferentially less than 0.5% by weight, relative to the total weight of said dye composition.

Advantageously, the assembly according to the invention is stored at a temperature of less than or equal to 0° C., preferably between −80° C. and 0° C.; and/or in a container, such as a bag, away from atmospheric oxygen, that is to say under vacuum or under an inert atmosphere, preferably under nitrogen or argon.

II. Dispensing Means

A subject of the present invention is also a means for dispensing the assembly, as defined previously.

The assembly dispensing means may also comprise a rotary feed drum, in which the assembly as described previously is wound onto the revolving surface of said rotary feed drum, or one of the ends of the assembly is held in a radial groove of said drum.

This rotary feed drum may be made of plastic, metal or wood, preferably plastic.

Said rotary feed drum may be rotated manually by the user, or by means of an electric motor.

Thus, when said drum is rotated such that said assembly partially unwinds from said drum, the user can then grasp the assembly and cut it, preferably along an axis parallel to the axis of rotation of said drum, to the desired length.

In this way, the user has an assembly at the correct size that he or she wishes to use, and thus avoids any wastage of said assembly.

The user may in particular cut the assembly by tearing, by ripping, by using a pair of scissors, by using a knife or by using a cutting means.

Advantageously, the dispensing means comprises a means for cutting said assembly.

More preferentially, the means for cutting said assembly is chosen from a guillotine or a serrated blade.

III. Process for Dyeing Keratin Fibres

A subject of the present invention is also a process for the oxidation dyeing of keratin fibres, in particular human keratin fibres such as the hair, comprising:
 i) a step consisting in removing said protective substrate(s) from the assembly according to the invention;
 ii) a step of applying, to said fibres, the dyeing substrate(s) as defined previously; and
 iii) a step of applying, to said fibres, an oxidizing aqueous composition comprising one or more chemical oxidizing agents, and optionally one or more alkaline agents.

As previously indicated, the process comprises a step during which the protective substrate(s) are removed from the assembly according to the invention.

In other words, the protective substrate(s) are separated from the dyeing substrate in order to use said substrate on the keratin fibres.

As indicated previously, the oxidation dyeing process uses an oxidizing aqueous composition containing one or more chemical oxidizing agents.

The term "chemical oxidizing agent" is intended to mean an oxidizing agent other than atmospheric oxygen.

Preferably, the chemical oxidizing agent(s) are chosen from hydrogen peroxide, urea peroxide, alkali metal bromates or ferricyanides, peroxygenated salts, for instance alkali metal or alkaline-earth metal persulfates, perborates and percarbonates, and also peracids and precursors thereof.

Even more preferentially, the chemical oxidizing agent(s) are chosen from hydrogen peroxide, peroxygenated salts, urea peroxide or alkali metal bromates or ferricyanides.

This oxidizing agent advantageously is constituted of hydrogen peroxide especially as an aqueous solution (aqueous hydrogen peroxide solution), the concentration of which may range more particularly from 0.1% to 50% by weight, even more preferentially from 0.5% to 20% by weight and better still from 1% to 15% by weight relative to the total weight of the oxidizing composition.

Preferably, the chemical oxidizing agents are chosen from hydrogen peroxide and/or peroxygenated salts.

Preferably, the oxidizing aqueous composition also contains one or more alkaline agents, especially the alkaline agents as described previously.

The use of an oxidizing aqueous composition containing one or more alkaline agents in the course of the dyeing process according to the invention can especially lead to a lightening effect on the treated keratin fibres.

This use is particularly advantageous for dyeing dark or chestnut-brown hair.

The oxidizing aqueous composition may also comprise one or more thickeners or viscosity regulators such as hydroxyalkylcelluloses, for instace hydroxyethylcellulose, especially sold by Ashland® under the reference Natrosol Plus 330.

The oxidizing aqueous composition may also comprise one or more oxidation dyeing couplers.

In this way, placing in contact the keratin fibres, the dyeing substrate as defined previously and the oxidizing aqueous composition containing one or more couplers will make it possible to lead to varied colourings, given that the coupler(s) present in the oxidizing composition will be able to react with the oxidation base(s) present on the dyeing substrate.

The use of an oxidizing aqueous composition containing one or more oxidation dyeing couplers is advantageous since it makes it possible to limit the use of the number of assemblies by varying the nature of the oxidizing composition, while at the same time increasing the possible results as regards the colour.

The use of an oxidizing aqueous composition containing one or more couplers thus makes it possible to obtain a wide range of colours.

According to a preferred embodiment of the invention, the oxidizing aqueous composition also comprises one or more alkaline agents and/or one or more oxidation dyeing couplers.

According to another preferred embodiment of the invention, the protective substrate(s) are removed from said assembly, then the keratin fibres are placed on the surface of the dyeing substrate bearing the oxidation dye(s); that is to say the place where the surface of the dyeing substrate is covered with a layer containing the oxidation dye(s); and the oxidizing aqueous composition is then applied to said keratin fibres. The oxidation dyes are thus dissolved, react with the oxidizing agent and dye the keratin fibres.

The oxidizing aqueous composition is especially applied using an applicator, in particular a brush, or by hand.

In accordance with this embodiment, after applying the oxidizing composition, the locks of hair thus treated may be protected with a paper to protect the other locks that have not been treated.

According to one variant of the invention, the oxidation dyeing process consists in applying an oxidizing aqueous composition, as described previously, containing one or more chemical oxidizing agents, to the keratin fibres, then in removing the protective substrate(s) from said assembly, then in applying, to said keratin fibres, the dyeing substrate(s) as defined previously.

In this embodiment, the order of application between the dyeing substrate(s) as defined previously and the oxidizing aqueous composition is thus inverted relative to the preceding embodiment.

The dyeing substrat(es) comprising one or more oxidation dyes may be applied to the keratin fibres for a time ranging from 5 to 60 minutes and preferably ranging from 10 to 30 minutes.

The oxidizing aqueous composition may be applied to the keratin fibres for a time ranging from 5 to 60 minutes and preferably ranging from 10 to 30 minutes.

The dyeing substrate(s) and the oxidizing aqueous composition may be applied at ambient temperature (25° C.), optionally with raising of the temperature, which may be up to 60° C.

After the treatment, the human keratin fibres are optionally rinsed with water, optionally washed with a shampoo and then rinsed with water, before being dried or left to dry.

EXAMPLES

Dye compositions C1 land C2 for treating the surface of the dyeing substrate according to the invention are prepared from the ingredients shown in the table below, the amounts of which are expressed as weight percentages of active material (AM).

| Ingredients | Composition C1 | Composition C2 |
|---|---|---|
| 2,5-Toluenediamine | 4 | |
| 4-(2-Hydroxyethoxy)-1,3-phenylenediamine dihydrochloride | 7.9 | |
| (C14/C16) Alkyl hydroxyethylcellulose | | 1 |
| Erythorbic acid | — | 0.3 |
| Thiolactic acid | — | 0.4 |
| Water | qs 100 | qs 100 |

A composition P1 of preservatives for treating the surface of the protective substrates according to the invention is also prepared from the ingredients shown in the table below, the amounts of which are expressed as weight percentages of active material (AM).

| Ingredients | Composition P1 |
|---|---|
| Sodium bisulfite | 10 |
| Water | qs 100 |

Preparation of the Dyeing Substrates SC1:

840 mg of composition C1 are applied uniformly using a HandCoater (sold by RK PrintCoat Instruments Ltd., K-HandCoater range, under the reference "yellow") on a 20×10 cm dyeing substrate of parchment paper type. The deposit of dye composition C1 is thus 4.2 mg/cm$^2$ before drying.

The dyeing substrate SC1 is then dried.

Preparation of the Dyeing Substrates SC2:

The dyeing substrate SC2 is prepared in the same way as SC1, but with 840 mg of composition C2 instead of 840 mg of composition C1.

Preparation of the Protective Substrate SPi According to the Invention:

840 mg of composition P1 are applied uniformly using a HandCoater (sold by RK PrintCoat Instruments Ltd., K-HandCoater range, under the reference "yellow") on a 20×10 cm protective substrate of white stationery paper type. The deposit of the composition is thus 4.2 mg/cm$^2$ before drying.

The protective substrate SPi is then dried, and 840 mg of composition P1 are again applied uniformly using a Hand-Coater on the back side of the protective substrate.

Preparation of the Oxidizing Composition:

The oxidizing composition is a L'Oréal "2" 30 V Oxidizing Creme, equivalent to 9 volumes of hydrogen peroxide.

Example 1

An assembly A1 (invention) which comprises a dyeing substrate SC1 and two protective substrates SPi is prepared, the two protective substrates SPi being in direct contact with SC1 and placed on either side of SC1. In other words, the assembly A1 is a superposition of the dyeing substrate SC1 and of the two protective substrates SPi, where the dyeing substrate SC1 is between the two protective layers.

An assembly A2 (invention) which comprises a dyeing substrate SC1 and a protective substrate SPi is prepared, the protective substrate SPi being directly in contact with SC1 and covering SC on the surface treated with the composition C1.

An assembly A3 (outside the invention), which comprises a dyeing substrate SC1, without protective substrate, is prepared.

The three assemblies A1, A2 and A3 are then bagged, independently of one another. The three bags are then placed under vacuum and, finally, placed under an inert atmosphere by filling with argon.

The bags are then stored at atmospheric pressure and ambient temperature for 4 weeks.

The three bags are then opened and the assemblies A1, A2 and A3 are used according to the following dyeing process:
1) for A1 and A2, the protective substrate(s) SPi are removed from the assembly, then
2) 1.5 g of grey hair containing 90% white hairs are deposited on the dyeing substrate SC1, then
3) the oxidizing composition is applied to the lock of hair deposited on SC1, then 4) the lock is left to stand for 30 minutes and, finally
5) the lock is rinsed, washed with a shampoo and rinsed with water.

After drying the locks of hair, an intense blue colour judged to be satisfactory is observed for the locks of hair treated with the assembly A1 or the assembly A2.

A pale blue colour judged to be unsatisfactory is also observed for the lock of hair treated with the assembly A3.

Example 2

An assembly A4 (invention) which comprises a dyeing substrate SC2 and two protective substrates SPi is prepared, the two protective substrates SPi being in direct contact with SC2 and placed on either side of SC2. In other words, the assembly A4 is a superposition of the dyeing substrate SC2 and of the two protective substrates SPi, where the dyeing substrate SC2 is between the two protective layers.

An assembly A5 (invention) which comprises a dyeing substrate SC2 and a protective substrate SPi is prepared, the protective substrate SPi being directly in contact with SC2 and covering SC2 on the surface treated with the composition C2.

An assembly A6 (outside the invention), which comprises a dyeing substrate SC2, without protective substrate, is prepared.

10 assemblies A4 are then bagged together, as are, in the same way, 10 assemblies A5 and 10 assemblies A6. The three bags are then placed under vacuum and, finally, placed under an inert atmosphere by filling with argon and sealed by thermal welding.

The bags are then stored at atmospheric pressure and ambient temperature for 4 weeks.

The three bags are then opened and 5 assemblies, from each bag, are used according to the following dyeing process:
1) for A4 and A5, the protective substrate(s) SPi are removed from the assembly, then
2) 1.5 g of grey hair containing 90% white hairs are deposited on the dyeing substrate SC2, then
3) the oxidizing composition is applied to the lock of hair deposited on SC2, then
4) the lock is left to stand for 30 minutes and, finally
5) the lock is rinsed, washed with a shampoo and rinsed with water.

After drying the locks of hair, an intense blue colour judged to be satisfactory is observed for the locks of hair treated with the assembly A4 or the assembly A5.

A pale blue colour judged to be unsatisfactory is also observed for the lock of hair treated with the assembly A6.

Three days after opening the bags, the 5 other assemblies from each bag are used according to the same dyeing process.

After drying the locks of hair, an intense blue colour judged to be satisfactory is observed for the locks of hair treated with the assembly A4 or the assembly A5.

A pale blue colour judged to be unsatisfactory is also observed for the lock of hair treated with the assembly A6.

Example 3

An assembly A5 (invention) as prepared in Example 1 above, is prepared.

An assembly A7 (outside the invention) which comprises a dyeing substrate SC2 and a comparative protective substrate SPc is prepared, the comparative protective substrate SPc being directly in contact with SC2 and covering SC2 on the surface treated with the composition C2.

The comparative protective substrate SPc corresponds to a simple 20×10 cm sheet of white stationery paper type. In other words, the comparative protective substrate SPc corresponds to the protective substrate SPi according to the invention as described above without the deposit on its surface of the composition P1.

Each assembly A5 and A7 is then bagged, independently of one another, just after their preparation.

The two bags are then placed under vacuum and, finally, placed under an inert atmosphere by filling with argon and sealed by thermal welding.

The two bags are then stored at atmospheric pressure and ambient temperature for 4 weeks.

After 4 weeks, the two bags are then opened and each assembly is used according to the following dyeing process:
1) the protective substrate SPi are removed from the assembly A5 and the protective substrate SPc are removed from the assembly A7, then
2) 1.5 g of grey hair containing 90% white hairs are deposited on the dyeing substrate SC2, then
3) the oxidizing composition is applied to the lock of hair deposited on SC2, then
4) the lock is left to stand for 30 minutes and, finally
5) the lock is rinsed, washed with a shampoo and rinsed with water.

After drying the locks of hair, an intense blue colour judged to be satisfactory is observed for the locks of hair treated with the assembly A5 according to the invention.

A pale blue colour judged to be unsatisfactory is also observed for the lock of hair treated with the comparative assembly A7 (outside the invention).

Example 4

A dyeing substrate in paper sheet form is prepared by flexography, using the Anilox GTT28 $cm^3/cm^2$.

The dyeing substrate is then dried by infrared at the printing outlet. The amount of ink deposited is approximately 1 mg of ink per $cm^2$ of substrate per passage. The ink used containing approximately 12% of oxidation dyes, i.e. 0.12 mg of oxidation dyes deposited per $cm^2$ of substrate per passage.

The substrate flow rate is 10 metres per minute.

Example 5

One particular embodiment of a dispensing means according to the invention is represented according to the appended FIG. 1.

Figure 1:
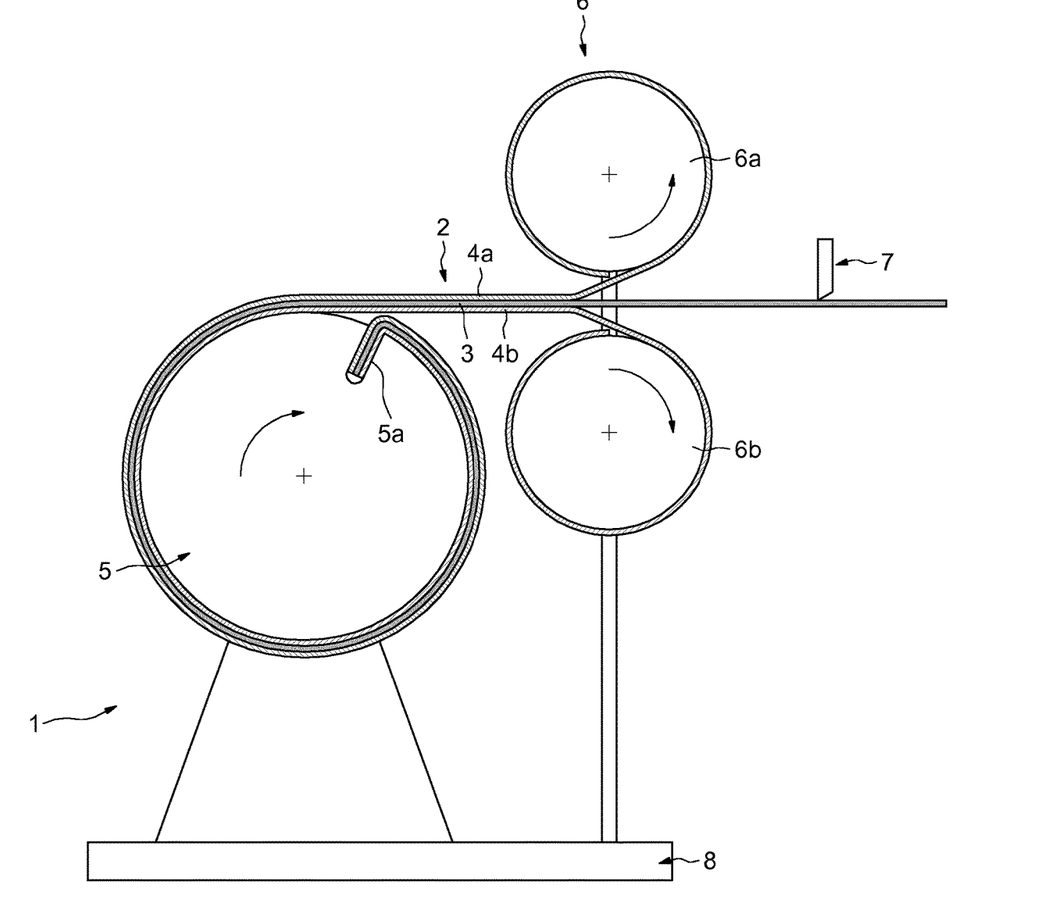
FIG. 1 represents a sectional view of a dispensing means according to the invention in accordance with one particular embodiment.

FIG. 1 represents a means for dispensing 1 the assembly 2 comprising a dyeing substrate 3 placed between two protective substrates 4a and 4b and in contact with said substrates. In other words, the dyeing substrate 3 is sandwiched between the two protective substrates 4a and 4b.

The dispensing means 1 comprises a rotary feed drum 5 which has a substantially circular profile and on which the assembly 2 is wound. The assembly 2 can be directly in contact with the rotary feed drum 5. In particular, the assembly 2 is held in a groove 5a of the drum 5.

The dispensing means 1 also comprises a separating means 6 intended to detach the protective substrates 4a and 4b from the dyeing substrate 3, and a cutting means 7, preferably a serrated blade.

The dispensing means 1 is mounted on a support 8.

According to FIG. 1, the means for separating the two protective substrates from the dyeing substrate is constituted of two auxiliary rotary drums 6a and 6b placed one above the other along a vertical axis, such that, when the assembly 2 unwinds from the rotary feed drum 5, the assembly 2 passes between the two auxiliary drums 6a and 6b, the axes of rotation of which are parallel to the axis of rotation of the rotary feed drum.

According to FIG. 1, the two protective substrates, as defined previously, are attached to the auxiliary drums 6a and 6b by the user, and thus, when the rotary feed drum 5 is rotated such that the assembly 2 partially unwinds from the feed drum 5, the user can then grasp the dyeing substrate 3, optionally covered with a layer, termed "polymer" layer, as described previously, and can cut said substrate using the cutting means 7, preferably a serrated blade, along an axis parallel to the axis of rotation of the rotary feed drum 5, to the desired length.

FIG. 1 thus represents in particular a means for dispensing 1 the assembly 2 as described previously, comprising a means for separating 6 the two protective substrates 4a, 4b from the dyeing substrate 3, and a means for cutting 7 said dyeing substrate 3.

The dyeing substrate can then be applied to the keratin fibres for the time required for the dyeing.

An oxidizing aqueous composition as described previously can then be applied, in turn, to the keratin fibres in order to obtain the hair colouring desired by the user.

The invention claimed is:

1. Assembly containing:
   at least one substrate for dyeing keratin fibres, comprising a surface coated with at least one layer constituted of a dye composition comprising one or more oxidation dyes; and
   at least one protective substrate, comprising a surface coated with at least one layer constituted of a composition comprising one or more preservatives;
   it being understood that said dyeing substrate(s) are different from said protective substrate(s).

2. Assembly according to claim 1, characterized in that the dyeing substrate is in contact with at least one protective substrate.

3. Assembly according to claim 2, characterized in that the dyeing substrate is included between two protective substrates.

4. Assembly according to claim 1, characterized in that a protective substrate partially or totally envelops the dyeing substrate.

5. Assembly according to claim 1, characterized in that the dyeing substrate(s) are elements in sheet form.

6. Assembly according to claim 5, characterized in that the element in sheet form is made of plastic, paper, metal, a woven, a nonwoven of non-absorbent fibres, or polyamide 6,6.

7. Assembly according to claim 5, characterized in that the element in sheet form comprises an adhesive layer on which is (are) deposited the oxidation dye(s).

8. Assembly according to claim 1, characterized in that the oxidation dye(s) are chosen from oxidation bases and optionally couplers.

9. Assembly according to claim 8, characterized in that the oxidation bases are chosen from para-phenylenediamines, bis(phenyl)alkylenediamines, para-aminophenols, ortho-aminophenols and heterocyclic bases, the addition salts thereof and mixtures thereof.

10. Assembly according to claim 8, characterized in that the couplers are chosen from meta-phenylenediamines, meta-aminophenols, meta-diphenols, naphthalene-based couplers and heterocyclic couplers, the addition salts thereof and mixtures thereof.

11. Assembly according to claim 1, characterized in that the preservative(s) are chosen from sulfites, bisulfites, sulfinates, sugars, hydrides, thiolated sulfur-bearing reducing agents, organic reducing agents of reductone type, agents capable of slowing down the oxidative condensation reaction, and mixtures thereof.

12. Assembly according to claim 1, characterized in that the preservative(s) are chosen from ammonium sulfites and bisulfites, alkali metal or alkaline-earth metal sulfites and bisulfites, reductic acid, ascorbic acid, erythorbic or isoascorbic acid, thioglycolic acid, thiolactic acid, cysteine, cysteamine, ethylenediaminotetraacetic acid (EDTA), citric acid, and mixtures thereof.

13. Assembly according to claim 1, characterized in that the preservative(s) are present in a total amount ranging from 0.1% to 60% by weight, relative to the total weight of the composition comprising the preservative(s).

14. Means for dispensing the assembly as defined in claim 1, comprising a means for cutting said assembly.

15. Means for dispensing the assembly as defined in claim 1 comprising a means for separating the two protective substrates from the dyeing substrate, and a means for cutting said dyeing substrate.

16. Process for the oxidation dyeing of keratin fibres, using an assembly according to claim 1, the process comprising:
   i) a step consisting in removing said protective substrate(s) from the assembly;
   ii) a step of applying, to said fibres, the dyeing substrate(s); and
   iii) a step of applying, to said fibres, an oxidizing aqueous composition comprising one or more chemical oxidizing agents.

* * * * *